(12) United States Patent
Van Dalen et al.

(10) Patent No.: US 8,683,613 B2
(45) Date of Patent: Apr. 1, 2014

(54) EYE PATCH

(75) Inventors: Johan T. W. Van Dalen, Tucson, AZ (US); Dan D. Carda, Tucson, AZ (US)

(73) Assignee: Eye Care and Cure Pte. Ltd, Singapore (SG)

( * ) Notice: Subject to any disclaimer, the term of this patent is extended or adjusted under 35 U.S.C. 154(b) by 306 days.

(21) Appl. No.: 13/208,726

(22) Filed: Aug. 12, 2011

(65) Prior Publication Data

US 2012/0036609 A1    Feb. 16, 2012

Related U.S. Application Data

(60) Provisional application No. 61/373,207, filed on Aug. 12, 2010.

(51) Int. Cl.
*A61F 9/04* (2006.01)
*A61F 9/06* (2006.01)

(52) U.S. Cl.
USPC .......................... 2/13; 2/12; 2/15; 2/10; 2/11

(58) Field of Classification Search
CPC ..................................... A61F 9/04; A42B 1/06
USPC ............. 2/171, 183, 174, 202, 203, 208, 209, 2/195.2; 132/273, 275; 128/864, 866
See application file for complete search history.

(56) References Cited

U.S. PATENT DOCUMENTS

| | | | | |
|---|---|---|---|---|
| 971,372 A | * | 9/1910 | Hamilton | 2/13 |
| 1,702,548 A | * | 2/1929 | Schloz | 192/25 |
| 4,582,401 A | * | 4/1986 | Grindle | 351/45 |
| 5,402,189 A | * | 3/1995 | Gill | 351/44 |
| 5,927,279 A | | 7/1999 | Oviatt | |
| 6,582,073 B1 | * | 6/2003 | Hayes et al. | 351/45 |
| 6,990,981 B2 | * | 1/2006 | DuBois et al. | 128/858 |
| 7,318,440 B1 | | 1/2008 | Grijalva | |
| 8,418,695 B1 | * | 4/2013 | Moulton | 128/858 |

* cited by examiner

*Primary Examiner* — Gloria Hale
(74) *Attorney, Agent, or Firm* — Dale F. Regelman; Quarles & Brady LLP

(57) ABSTRACT

An eye patch is presented that is usable with eyeglass frames comprising a lens and side arm. The eye patch comprises a conoidal member to be positioned over a front of the lens such that a frontal and a peripheral vision of an eye is substantially blocked and a flap having a releasable securing device, wherein the flap is to be positioned over a back of the lens such that the releasable securing device secures the eye patch to the eyeglass frames.

20 Claims, 6 Drawing Sheets

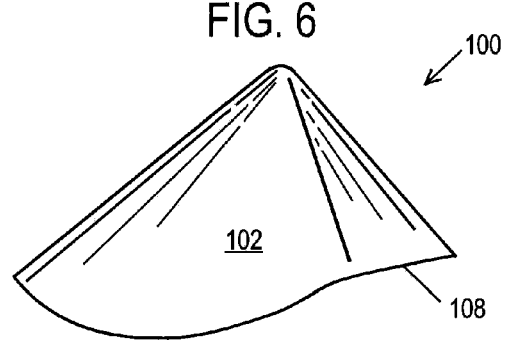
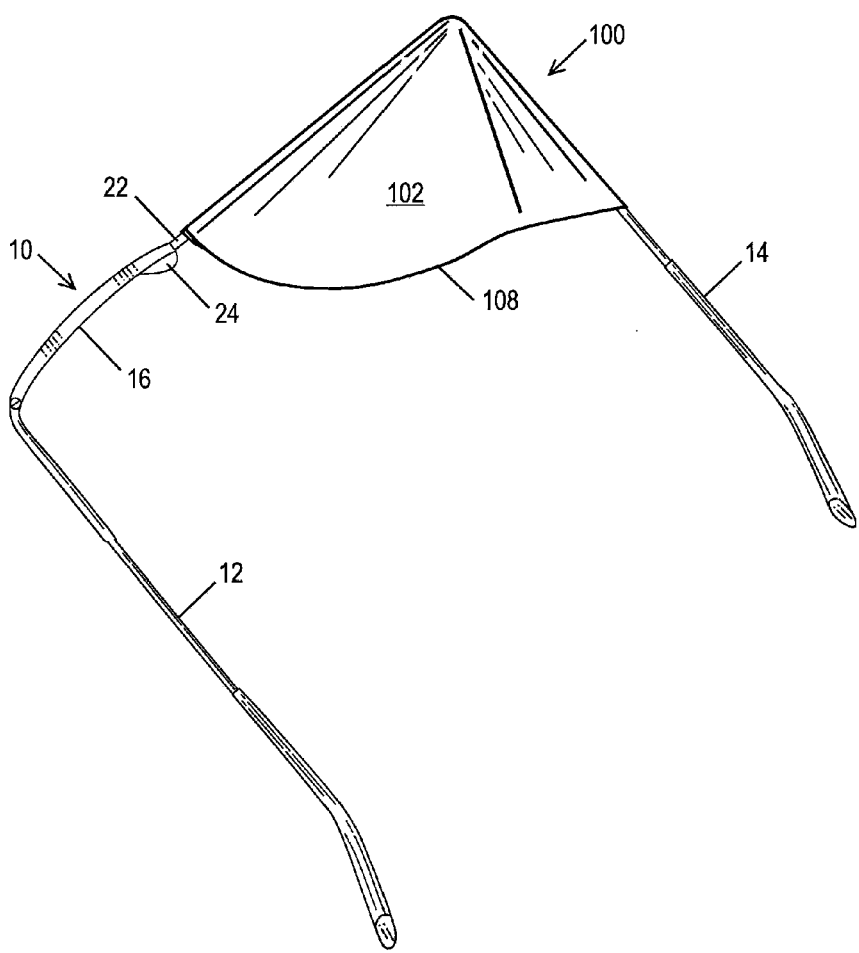

EYE PATCH

CROSS REFERENCE TO RELATED APPLICATIONS

This Application claims priority from a U.S. Provisional Application No. 61/373,207 filed Aug. 12, 2010, which is hereby incorporated by reference herein.

FIELD OF USE

The present invention relates generally to medical devices and more particularly to eye patches.

BACKGROUND

Ocular dominance, sometimes referred to as eye dominance or eyedness, is the tendency to prefer visual input from one eye over the other. While it is not uncommon for one eye to be dominant over the other, an overwhelming dominance can be harmful and can lead to a loss of vision in the weaker eye. For young children, the strength of the weaker eye may be improved by placing an eye patch over the dominant eye, thereby forcing reliance on the weaker eye.

To effectively rehabilitate the weaker eye, a child must be prevented from using his or her peripheral vision to see out of the dominant eye. Thus, sight lines of the dominant eye are generally blocked by using an eye patch that is secured with an adhesive to the child's face over the dominant eye. This arrangement has numerous disadvantages however. Such eye patches are often uncomfortable for the child and the adhesive may irritate the child's skin and eyebrow. Perspiration can increase these effects as it can cause itching and the eye patch may come loose, increasing the frequency at which it is re-adhered to the child's face. The close proximity of the eye patch to the eye may also cause irritation.

SUMMARY

In one implementation, an eye patch is presented that is usable with eyeglass frames comprising a lens and side arm. The eye patch comprises a semi-rigid conoidal member to be positioned over a front of the lens such that a frontal and a peripheral vision of an eye is substantially blocked and a flap having a releasable securing means, wherein the flap is to be positioned over a back of the lens such that the releasable securing means secures the eye patch to the eyeglass frames. By substantially blocked, Applicants mean that at least 95% of the vision of the eye is blocked.

In another implementation, an assembly is presented, where the assembly comprises an eyeglass frame having a lens and side arm and an eye patch. The eye patch includes a semi-rigid conoidal member to be positioned over a front of the lens such that a frontal and a peripheral vision of an eye is substantially blocked and a flap having a releasable securing means, wherein the flap is to be positioned over a back of the lens such that the releasable securing means secures the eye patch to the eyeglass frames.

BRIEF DESCRIPTION OF THE DRAWINGS

Implementations of the invention will become more apparent from the detailed description set forth below when taken in conjunction with the drawings, in which like elements bear like reference numerals.

FIG. 6 is a top view of Applicants' eye patch;

FIG. 7 is a top view of Applicants' eye patch mounted to a pair of eyeglass frames;

DETAILED DESCRIPTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

U.S. Pat. No. 5,927,279 teaches an eye patch having a fabric body that attaches to the nose pad of an eyeglass frame and includes a slot that the arm of the frame extends through. One difficulty with the eye patch taught by Oviatt is that the eye patch is still in close proximity to the eye and may cause irritation. Additionally, repeated attaching and removing of the eye patch from the eyeglass frames can damage or break the nose pad. Further, such an eye patch can only be used with glasses frames having a certain style of nose pad and cannot be used with those without nose pads, such as plastic frames, or those that have nose pads that are molded to the frames or made in a continuous piece.

U.S. Pat. No. 7,318,440 to Grijalva teaches a flexible eye patch having at least a first fastener that secures one end of the eye patch to a side arm of the glasses frames and a second fastener that attaches the second end to the bridge of the frames. The eye patch may additionally have a third fastener that secures the middle of the eye patch to the corner of the eye glass frames. However, such fasteners can be difficult for small children to use which may lessen the child's compliance with wearing the eye patch. Additionally, the fasteners may have sharp edges that can scratch and irritate a child's skin, thereby also making compliance less likely.

Figure 3A:
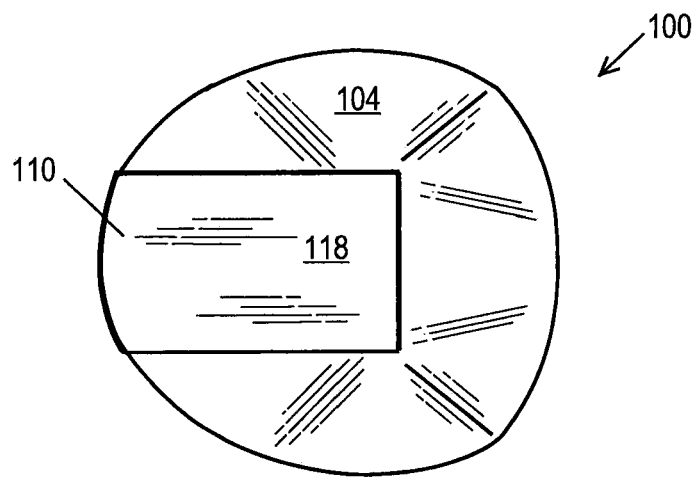
FIG. 3A is a back view of Applicants' eye patch with the securing means closed.
Figure 3B:
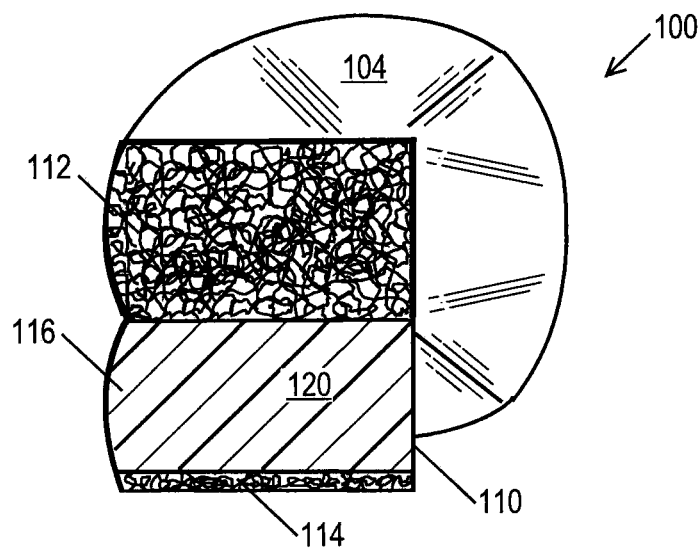
FIG. 3B is an alternative view of the back of Applicants' eye patch with the securing means open.
Figure 3C:
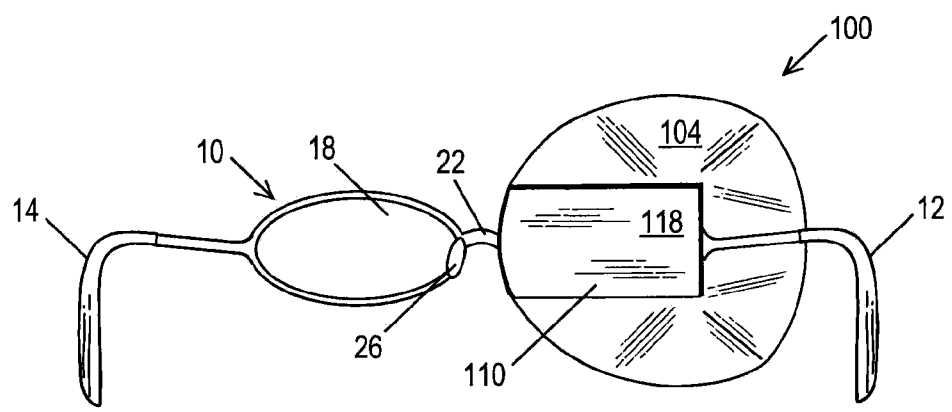
FIG. 3C is a back view of Applicants' eye patch mounted to a pair of eyeglass frames.

Applicants' invention overcomes the deficiencies of the prior art described above. Referring now to FIGS. 1-7, an embodiment of Applicants' eye patch 100 is presented for blocking the frontal and peripheral vision of an eye. In the illustrated embodiment of FIG. 1, Applicants' ambi-orientational eye patch 100 is shown mounted on eyeglass frame 10 comprising side arms 12 and 14, lenses 16 and 18 (FIGS. 3C and 7), bridge 22, and nose pieces 24 (FIGS. 4 and 7) and 26 (FIG. 3C). A frontal view of eye patch 100 is presented in FIG. 2. By ambi-orientational, Applicants' mean that eye patch 100 can be used over either the left eye or the right eye without altering eye patch 100 in any way. As can be seen in the illustrated embodiment of FIG. 1, eye patch 100 comprises a semi-rigid conoidal body 108 having securing means 110 (FIGS. 3A and 3B). The cone shape of body 108 can also be seen in FIG. 6, which depicts a top view of eye patch 100. By semi-rigid Applicants mean that body 108 retains its shape but will flex when a force is applied.

Figure 1:
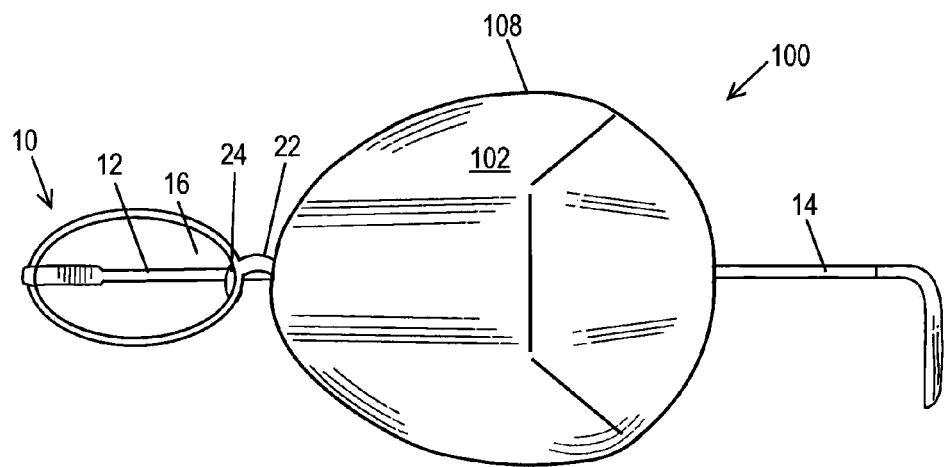
FIG. 1 is a perspective view of Applicants' eye patch mounted to a pair of eyeglass frames.
Figure 2:
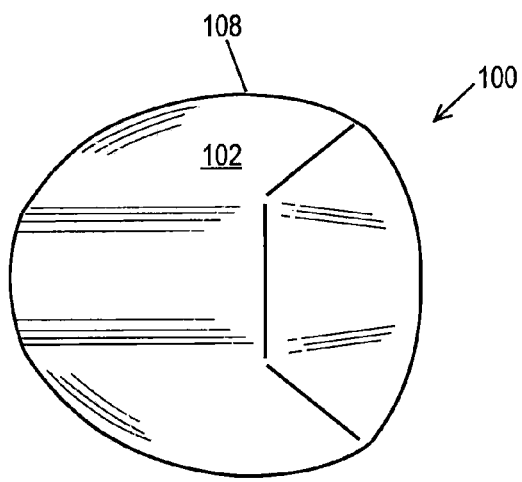
FIG. 2 is a front view of Applicants' eye patch.

In the illustrated embodiment of FIG. 1, body 108 comprises exterior member 102 and interior member 104 (FIGS. 3A, 3B, and 9) each comprising a flexible material that retains a conoidal shape when assembled and that is either singularly or collectively substantially opaque. By substantially opaque, Applicants mean that the front of eye patch 100 blocks at least 95% of light. In certain embodiments, interior member 104 comprises a non-abrasive material, such as, by way of example and not limitation, fabric, felt, acrylic, or vinyl. In certain embodiments, exterior member 102 comprises a different material than interior member 104. In such embodiments, exterior member 102 may be decorative, and may incorporate decorative designs or fabrics.

Figure 8:
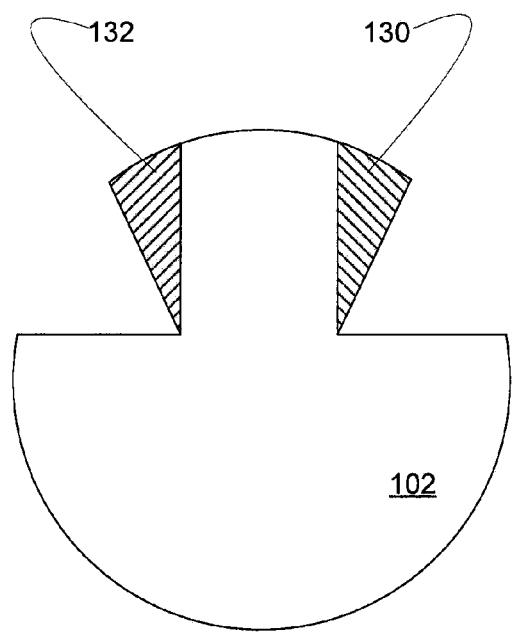
FIG. 8 is a schematic of the exterior surface of Applicants' eye patch.
Figure 9:
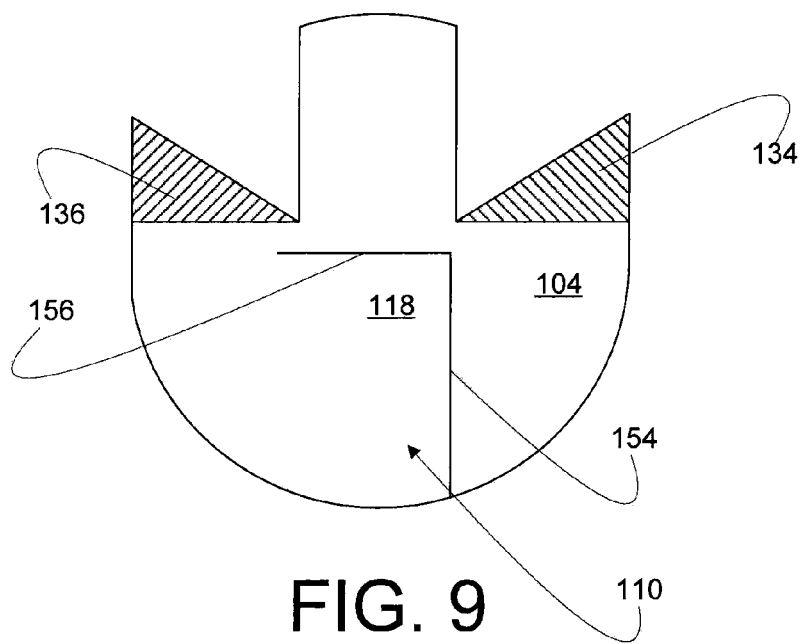
FIG. 9 is a schematic of the interior surface of Applicants' eye patch.

Unassembled exterior member 102 is depicted in FIG. 8 and unassembled interior member 104 is depicted in FIG. 9. As is shown in the illustrated embodiment of FIG. 8, exterior member 102 comprises joining members 130 and 132. Likewise, as is shown in the illustrated embodiment of FIG. 9, interior member 104 comprises joining members 134 and 136. When formed into the cone shape of body 108, joining member 130 is positioned over and secured to joining member 134 and joining member 132 is positioned over and secured to joining member 136. In certain embodiments, joining member 130 may be secured to joining member 134 using glue. In such embodiments, the glue may comprise, by way of example and not limitation, vegetable glues, resin cements, protein glues, latex cements, thermal adhesives, two part adhesives, such as epoxies, polyurethanes, acrylics, or silicon's, moisture cure adhesives, such as silicon's or polyurethanes, ultraviolet cure adhesives, cyanoacrylate adhesives, anaerobic adhesives, or film adhesives. In other embodiments, joining member 130 may be secured to joining member 134 by sewing, molding, or otherwise fabricating joining members 130 and 134 together. In other embodiments, joining member 130 may be secured to joining member 134 using snaps, hook and loop fasteners, or other releasable securing means.

Interior member 104 is further cut along edges 154 and 156 to form exterior surface 118 and interior surface 120 (FIG. 3B) of securing means 110.

In certain embodiments, other areas of interior member 104 are further secured to exterior member 102. In certain embodiments, all of interior member 104, except for the area forming securing means 110, is secured to exterior member 102. In certain embodiments, interior member 104 is further attached to exterior member 102 by glue. In other embodiments, interior member 104 is attached to exterior member 102 by sewing, molding, or otherwise fabricating interior member 104 to exterior member 102.

Figure 4:
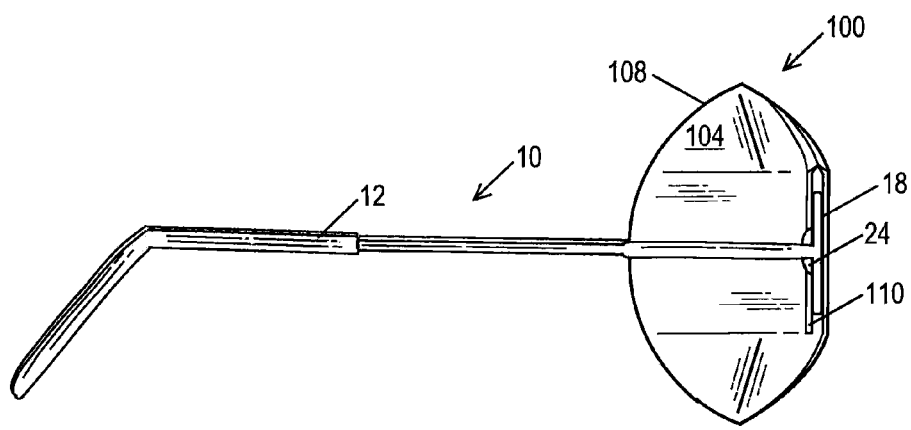
FIG. 4 is a side view of Applicants' eye patch mounted to a pair of eyeglass frames.
Figure 5:
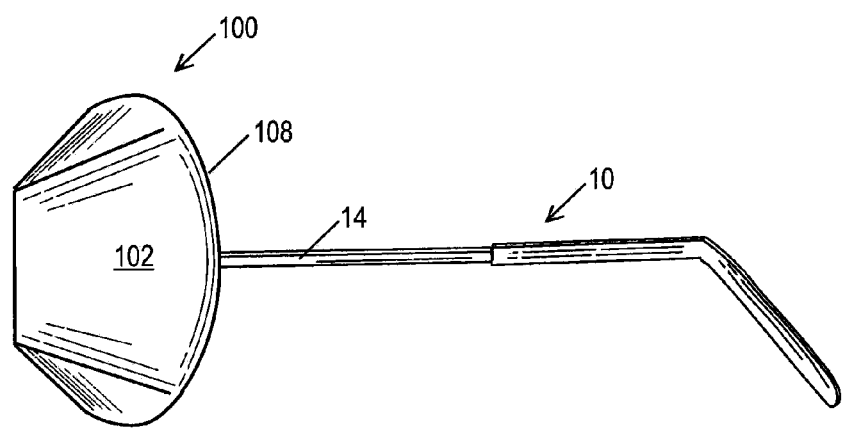
FIG. 5 is a side view of Applicants' eye patch mounted to a pair of eyeglass frames.

Turning to FIGS. 3A-3C, Applicants' ambi-orientational eye patch 100 attaches to eyeglass frame 10 via securing means 110. FIGS. 4, 5, and 7 provide additional views of eye patch 100 mounted on eyeglass frame 10. In the illustrated embodiment of FIGS. 3A-3C, securing means 110 is shown as a flap which can attach to interior member 104 via releasable attaching means 112 and 114. In certain embodiments, releasable attaching means 112 and 114 are a hook and loop fastening tape, such as, by way of example and not limitation, Velcro® brand hook and loop fastening tape by Velcro Industries, B.V. In other embodiments, releasable attaching means 112 and 114 comprise snaps, buttons, or any other type of releasable fastener.

In certain embodiments, releasable attaching means 114 extends over the entire surface of the interior surface 120 of securing means 110. In other embodiments, releasable attaching means 114 extends over only a portion of interior surface 120 of securing means 110. In such embodiments, the remaining portion of interior surface 120 may be the same as exterior surface 118 of securing means 110. In other such embodiments, the remaining portion of interior surface 120 may be different from exterior surface 118. In certain embodiments, the remaining portion of interior surface 120 may comprise a flexible, non-abrasive protective layer 116 to protect the lens, where protective layer 116 may be, for example and without limitation, felt, fabric, acrylic, or vinyl.

As can be seen in the illustrated embodiment of FIG. 3C, to mount Applicants' ambi-orientational eye patch 100 to eyeglass frame 10, lens 16 (not shown) is placed between attaching means 112 of interior member 104 and interior surface 120 of securing means 110. Securing means 110 is then closed and secured to interior member 104 via attaching means 112 and 114. As will be apparent to one of ordinary skill in the art, Applicants' eye patch 100 is ambi-orientational. Thus, Applicants' eye patch 100 can be mounted over either lens 16 or lens 18 (as is depicted in FIG. 1).

In certain embodiments, Applicants' eye patch 100 is adapted to fit to the user's face. In such embodiments, the edges of eye patch 100 are trimmed to fit the contours of the user's cheek, forehead, and nose such that eye patch 100 sits snugly to the user's face without gaps.

Applicants' ambi-orientational eye patch 100 as described above may offer one or more of the following advantages. As eye patch 100 attaches to eyeglass frame 10 by enclosing either lens, a feature common to all eyeglass frames, eye patch 100 can be used with all types of eyeglass frames, including those without nose pads, such as plastic frames worn by many children. Attachment around the lens additionally lessens the risk of damage to the eyeglass frames themselves, such as seen with prior art eye patches that connect to the nose pad. Attachment is also easily performed by a young child, increasing the likelihood of compliance with a treatment plan. Further, as Applicants' eye patch 100 is ambi-orientational, a single eye patch can be used over either eye, making Applicants' eye patch less expensive for doctor's offices to stock.

As eye patch 100 is mounted onto eyeglass frame 10, there is no irritating adhesives to attach the eye patch directly to the face of the user, as with the prior art. Furthermore, the use of hook and loop fasteners alleviates the need for snaps or other attaching means which can have sharp edges and may be difficult for young children to manipulate. The semi-rigid cone shape of Applicants' ambi-orientational eye patch 100 also provides a greater degree of comfort to the wearer and lessens the risk that eye patch 100 will irritate the lashes, eyes, or skin. For additional comfort, Applicants' eye patch 100 may also be trimmed to fit the contours of the user's face. As Applicants' eye patch 100 may comprise washable materials, eye patch 100 may be easily cleaned to remove, dirt, sweat, and bacteria for repeated wearing.

While the preferred embodiments of the present invention have been illustrated in detail, it should be apparent that modifications and adaptations to those embodiments may occur to one skilled in the art without departing from the scope of the present invention.

What is claimed is:

1. An eye patch usable with eyeglass frames comprising a lens and a side arm, the eye patch comprising:
   a conoidal member to be positioned over a front of the lens such that a frontal and a peripheral vision of an eye is substantially blocked, wherein the conoidal member comprises an interior member and an exterior member, wherein the interior member comprises a first material and the exterior member comprises a second material; wherein the first material and the second material differ;
   a first securing means disposed on said interior member; and
   a flap attached to and extending outwardly from said interior member, said flap having a second securing means attached to a distal end thereof, wherein the flap is configured to be positioned over a back of the lens such that the second securing means releaseably attaches to said first securing means to enclose said lens.

2. The eye patch of claim 1, wherein the first securing means in combination with the second securing means comprises a hook and loop fastener.

3. The eye patch of claim 1, wherein the first material is decorative.

4. The eye patch of claim 1, wherein the second material is non-abrasive.

5. The eye patch of claim 1, wherein the conoidal member is adapted to at least partially extend along the side arm.

6. The eye patch of claim 1, wherein the conoidal member is adapted to be fitted to a user.

7. The eye patch of claim 6, wherein the conoidal member is adapted to be trimmed to fit a user.

8. The eye patch of claim 1, wherein the conoidal member is ambi-orientational.

9. The eye patch of claim 1, wherein the conoidal member comprises a fabric.

10. The eye patch of claim 1, wherein the flap comprises a non-abrasive material.

11. An assembly, comprising:
    an eyeglass frame comprising a lens and a side arm; and
    an eye patch comprising:
       a conoidal member to be positioned over a front of the lens such that a frontal and a peripheral vision of an eye is substantially blocked, wherein the conoidal member comprises an interior member and an exterior member, wherein the interior member comprises a first material and the exterior member comprises a second material; wherein the first material and the second material differ;
       a first securing means disposed on said interior member; and
       a flap attached to and extending outwardly from said interior member, said flap having a second securing means attached to a distal end thereof, wherein the flap is configured to be positioned over a back of the lens such that the second securing means releaseably attaches to said first securing means to enclose said lens.

12. The eye patch of claim 11, wherein the first securing means in combination with the second securing means comprises a hook and loop fastener.

13. The eye patch of claim 11, wherein the first material is decorative.

14. The eye patch of claim 11, wherein the second material is non-abrasive.

15. The eye patch of claim 11, wherein the conoidal member is adapted to at least partially extend along the side arm.

16. The eye patch of claim 11, wherein the conoidal member is adapted to be fitted to a user.

17. The eye patch of claim 16, wherein the conoidal member is adapted to be trimmed to fit a user.

18. The eye patch of claim 11, wherein the conoidal member is ambi-orientational.

19. The eye patch of claim 11, wherein the conoidal member comprises a fabric.

20. The eye patch of claim 11, wherein the flap comprises a non-abrasive material.

* * * * *